United States Patent [19]

Sirota

[11] Patent Number: 4,672,975
[45] Date of Patent: Jun. 16, 1987

[54] STETHOSCOPE WITH IMAGE OF PERIODICALLY EXPANDING AND CONTRACTING HEART

[76] Inventor: Vladimir Sirota, 130 W. 67 St., New York, N.Y. 10063

[21] Appl. No.: 745,684

[22] Filed: Jun. 17, 1985

[51] Int. Cl.[4] ............................................. A61B 7/02
[52] U.S. Cl. ................................................. 128/715
[58] Field of Search ............... 128/660, 663, 687, 689, 128/695, 701, 710, 711, 712, 715, 1 C, 706, 905; 434/262, 266, 267, 269, 272, 310

[56] References Cited

U.S. PATENT DOCUMENTS

| | | | |
|---|---|---|---|
| 2,772,672 | 12/1956 | Losner | 128/695 |
| 2,794,298 | 6/1957 | Mason | 128/1 C |
| 3,140,710 | 7/1964 | Glassner et al. | 128/715 |
| 3,283,181 | 11/1966 | Johanson | 128/715 |
| 3,323,515 | 6/1967 | Foner et al. | 128/712 |
| 3,552,036 | 1/1971 | Mahler | 434/262 |
| 3,789,833 | 2/1974 | Bom | 128/660 |
| 3,797,129 | 3/1974 | Ravin et al. | 434/266 |
| 3,858,005 | 12/1974 | Marshall et al. | 128/715 |
| 3,994,282 | 11/1976 | Moulet | 434/266 |
| 4,091,549 | 5/1978 | Driller et al. | 434/272 |
| 4,124,022 | 11/1978 | Gross | 128/1 C |
| 4,170,717 | 10/1979 | Walshe | 128/715 |
| 4,312,358 | 1/1982 | Barney | 128/706 |

FOREIGN PATENT DOCUMENTS

| | | | |
|---|---|---|---|
| 8418 | 1/1982 | Japan | 128/710 |
| 921396 | 3/1963 | United Kingdom | 128/715 |

*Primary Examiner*—William E. Kamm

[57] ABSTRACT

A stethoscope has a body part, a display forming element, and an electronic device which forms on the display an image of expanding and contracting heart. Also, an electronic device which generates audio signals can be provided. The image and the audio signals can be formed without any connection with heart beat of a person whose heart activity is monitored, thus serving only entertaining and distracting purposes. On the other hand, the image and the audio signals can be formed in response to and in correspondence with heart beat of a person whose heart activity is monitored so as to provide an additional visual and audio information about his or her heart activity.

16 Claims, 11 Drawing Figures

STETHOSCOPE WITH IMAGE OF PERIODICALLY EXPANDING AND CONTRACTING HEART

BACKGROUND OF THE INVENTION

The present invention relates to stethoscopes.

The stethoscopes are widely known and used for heart monitoring of patients. The known stethoscopes provide an audio information to a physician about the heart activity of a patient. However, known stethoscopes are not provided with means for visually illustrating the results of heart monitoring by the stethoscope. This has certain disadvantages both for the physician and for the patient. The known stethoscopes also do not provide loud audio information accessible to a patient about the heart activity. Therefore, it is advisable to improve the known stethoscopes in the above mentioned directions so as to increase efficiency of perception of the information provided by the stethoscope, and also to increase attractiveness of the process of heart monitoring by means of the stethoscope, for example for younger patients of children.

SUMMARY OF THE INVENTION

It is therefore an object of the present invention to provide a stethoscope which avoids the disadvantages of the prior art.

More particularly, it is an object of the present invention is to provide a stethoscope which produces more information about heart activity than the existing stethoscopes, and is more attractive for patients.

In keeping with these objects and with others which will become apparent hereinafter, one feature of the present invention resides, briefly stated, in a stethoscope which has a body part, means forming a display, and electronic means forming on the display an image which periodically changes in accordance with a program and substantially immitates an expanding an contracting heart.

In accordance with the advantageous feature of the present invention, the electronic means operates in dependence on the heart beat sensed by a sensor in the inventive stethoscope. Still another feature of the present invention is that the heart beats of the patient can be transformed in loud audio sounds to be heard outside of the stethoscope.

The novel features of the present invention are set forth in particular in the appended claims. The invention itself, however, will be best understood from the following description of preferred embodiments which is accompanied by the following drawing.

DESCRIPTION OF PREFERRED EMBODIMENTS

Figure 1:
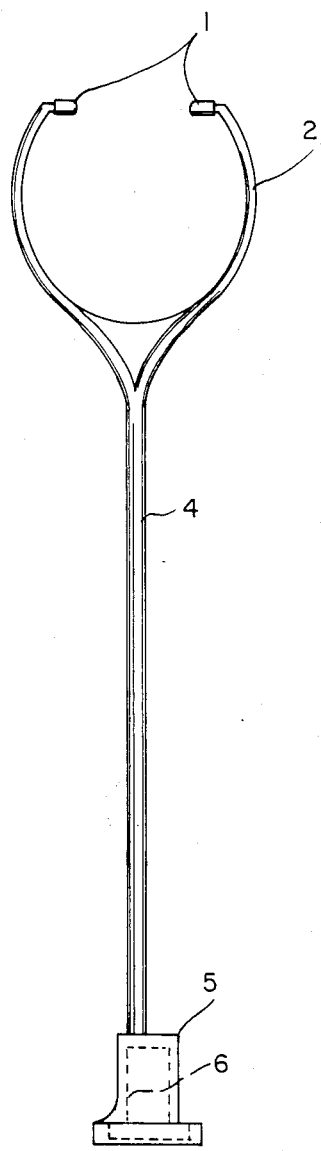
FIG. 1 is a view showing a general configuration of a stethoscope in which the present invention is employed.

FIG. 1 shows a stethoscope which has tips 1, earphones 2 and a plastic tube 4 with an enlarged end part 5. An electronic device 6 is arranged in the end part 5 as will be explained hereinbelow. The end part 5 has an opening 5' which is provided in its upper wall and communicates with the interior of the tube 4, and an opening 5" provided in its lower wall and communicating the interior of the end part 5 with its exterior, so that a sound passage is formed through the stethoscope.

Figure 2B:
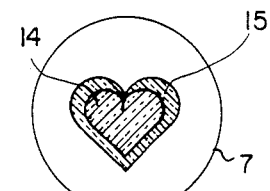
FIGS. 2a-2c are views showing one embodiment of an electronic device of the inventive stethoscope.
Figure 2A:
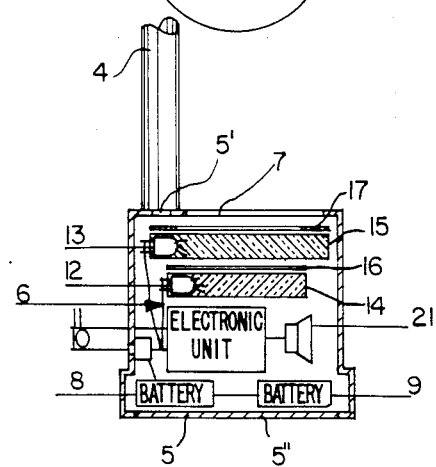
Figure 2C:
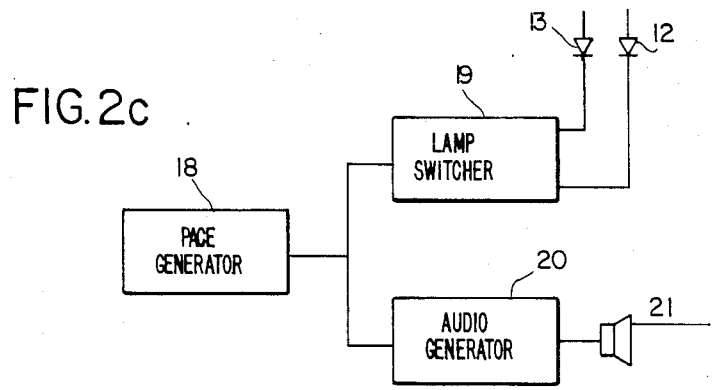

The electronic device is shown in FIGS. 2a-2c. It has a cover 7, two batteries 8 and 9 of watch type, a switch 10, an electronic unit 11, light emitting diodes 12 and 13, light conductors 14 and 15, and masks 16 and 17. The electronic unit 11 includes a pace generator 18, a lamp switcher 19, an audio generator 20 connected with a sonic transducer.

During conventional monitoring of heart activity of a patient, a physician turns on the switch 10 and the device starts to operate. The pace generator 18 produces rhythmic pulses of a square form, at about 70 cycles per min. These pulses control both the lamp switcher 19 and the audio generator 20. The lamp switcher 19 turns on either the light emitting diode 12 or 13, and turns them off. The diodes are located in colored plastic glass components 14 and 15. When either diode is on, it lights the whole area of the components. The masks are installed in front of the light conductors 14 and 15 and can be formed as a smaller heart and a bigger heart.

When either diode 12 or 13 is on, the smaller heart or the bigger heart will light. On the other hand, the smaller heart can always be on, while the greater heart can be alternatively on and off. This lighting of the conductors with the masks imitating expanding and contracting heart. It is to be understood that this imitating a discrete transmission from the smaller to the bigger heart and vice versa. It is also possible to provide more light conductors and masks, or to provide different means so as to imitating not discrete, but gradual expansion and contracting of a heart.

The pulses from the pace generator 18 also control the audio generator 20. This generator produces audio signals, about 800 cycles per sec. and operates the sound transducer 21 which generates loud audio signals during heart monitoring with the turned on switch 10. It is to be understood that the operation of the audio generator 20 can be synchronized with the lighting of the hearts. For example, the audio generator is on when only the bigger heart is on. It is also to be understood that the stethoscope can be provided only with the part of the electronic device which produces the video signals, without the audio signals. As can clearly be understood from FIGS. 2a-2c and the above presented description, the operation of the pulse generator and therefore of the diodes 12,13 and the audio generator 20 is not synchronized with actual heart beats of a patient whose heart activity is monitored by the stethoscope of the invention.

The image of expanding and contracting heart produced by the diodes 12,13 and the sounds produced by the audio generator 20 do not represent actual heart activity of a patient, but instead serve only the purpose of entertaining a patient and distracting him from the process of examination by the stethoscope. This is especially important for example for children who experience, as a rule, fear of doctors. Their attention will now be concentrated not on a physician who conducts the examination, but instead of the image of expanding and contracting heart and funny sounds.

Figure 3A:
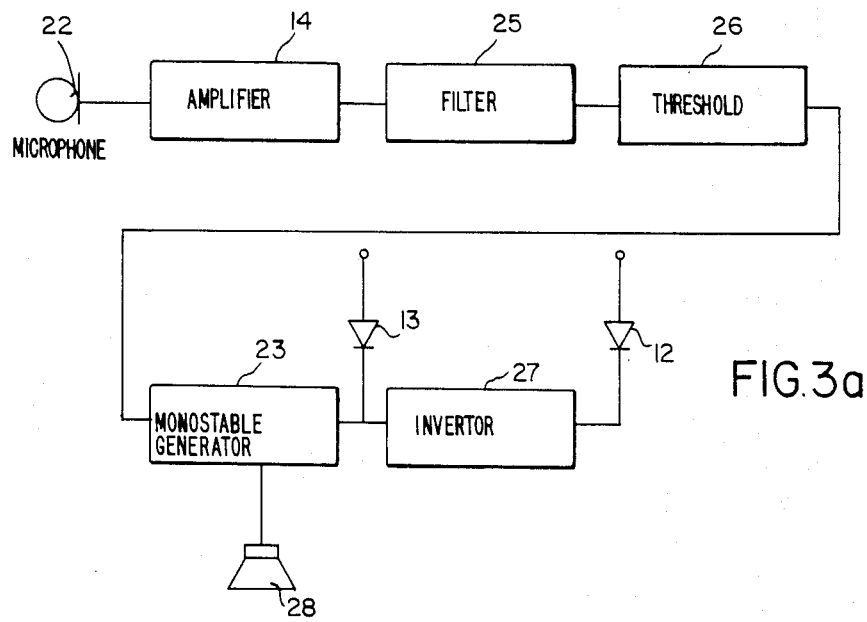
FIGS. 3a, 3b are views showing another embodiment of the electronic device.
Figure 3B:
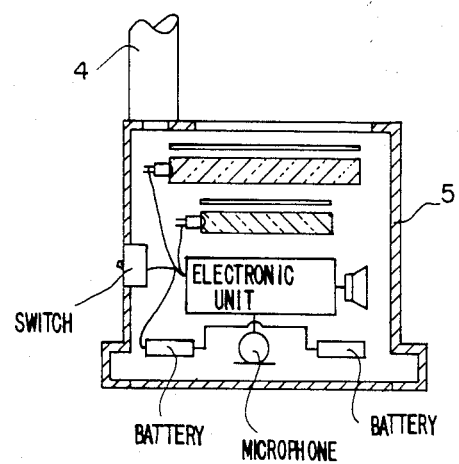

FIGS. 3a-3c show a stethoscope in which the image of expanding and contracting heart is formed in correspondence with heart beats of a patient. The stethoscope is provided with a microphone 22 which is connected with a monostable generator 23 through an amplifier 24, filter 25 and threshold circuit 26. The monostable generator 23 is connected with the light emitting diodes 12 and 13, and an inverter 27 is arranged between the diodes. The microphone 22 detects the heart beats and transforms them in electronic pulses supplied to the monostable generator 23 which control the time intervals of turning on and off of the diodes. The invertor 27 gurantees the alternating lighting of the diodes with the resulting lighting of the smaller and bigger hearts which is thereby performed synchronously with the heart beats of the patient. A sound generator 28 can also be provided in the electronic device to generate loud sounds in synchronism with the heart beats of the patient. Lighting of the small heart corresponds to the contraction of patient's heart, and lighting of the bigger heart corresponds to the expansion.

Figure 4:
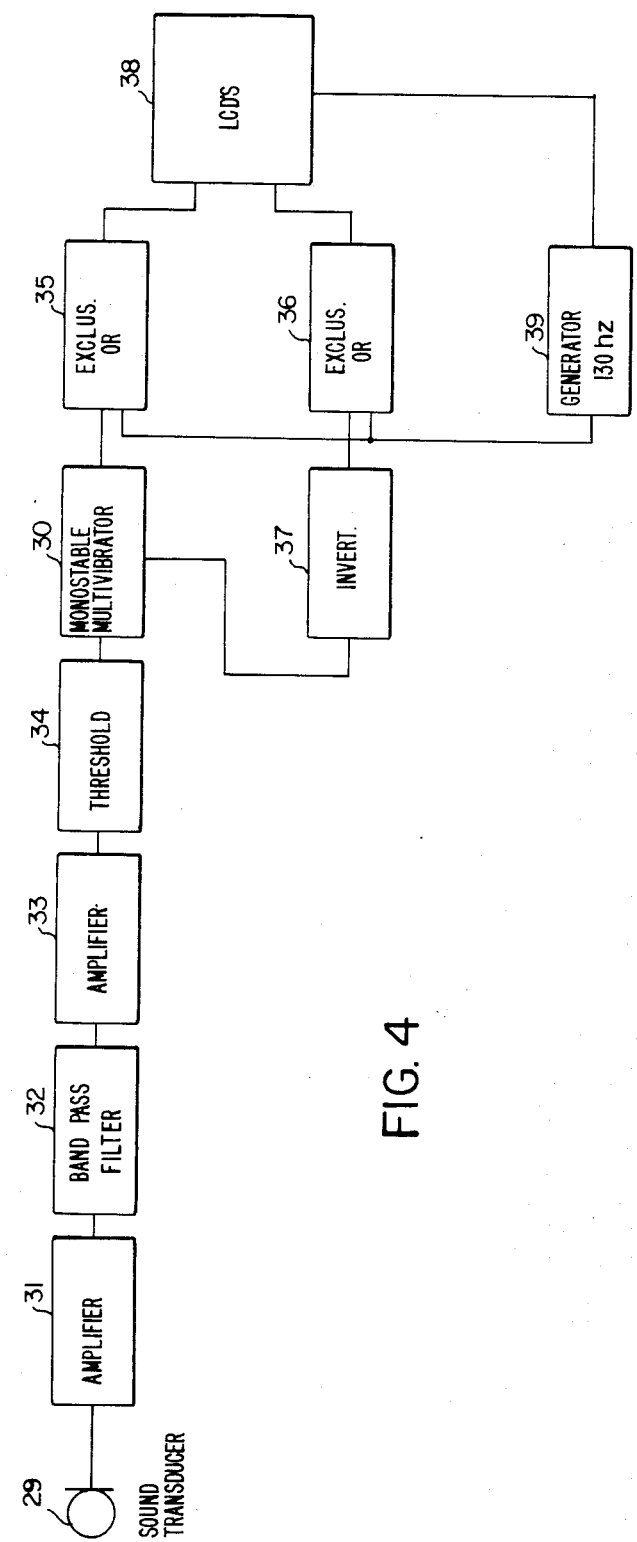
FIG. 4 shows a further embodiment of the electronic device of the inventive stethoscope.

FIG. 4 shows the electronic device for formation of the image and sound in synchronism with the heart beats, based on liquid crystals. A sound transducer 29 is connected with a monostable multivibrator 30 through an amplifier 31, band pass filter 32, an amplifier 33, threshold circuit 34. The monostable multivibrator 30 is connected with a first exclusive OR gate 35 directly, and with a second exclusive OR gate 36 via an inverter 37. The OR gates 35 and 36 are connected with a liquid crystal display 38. The OR gates 35 and 36, and the liquid crystal display 38 are supplied from a generator 39. It is believed that the operation of the device of FIG. 4 is understood. A changing image of a solid periodically expanding and contracting heart is formed on the liquid crystal display 38 in correspondence with the heart beats of a patient so as to represent actual heart activity of the patient. It is believed that the operation of the elements 31-34 and 24-26 are clear, since they conventionally amplify the respective signals, filter the signals from noise, limit their value etc. as known in the art. It is understood that in FIG. 4 the audio generator can also be included in the electronic device.

Figure 5:
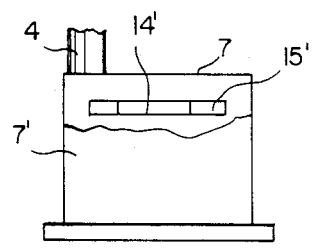
FIGS. 5 and 6 show two different arrangements of image producing elements of the inventive stethoscope.
Figure 6:
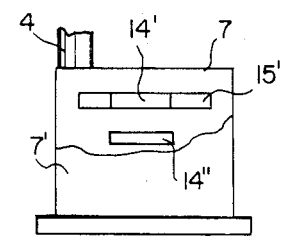

As can be seen from FIG. 1, 2a and 3b, the changing image of a heart is visible from above, to a physician who monitors the heart activity of the patient. The end of the plastic tube is somewhat offset from the center of the end part 5 so as not to obstruct the thus formed display on the upper surface of the end part. In the embodiment shown in FIG. 5, the light conductors 14' and 15' are located one behind the other as seen from the front side, and a side wall 7' is made transparent. Thereby, a patient can see the expanding and contracting heart easier. FIG. 6 shows that the image can be visible both to the patient and to the physician. Additionally to the light conductors 14' and 15', a smaller light conductor 14 is located therebelow. Both the cover 7 and the side wall 7' are made transparent. The changing image is visible from above to a physician through the cover 7 as a result of cooperation of the light conductors 15' and 14", and and from the side to a patient through the side wall 7' as a result of cooperation of the light conductors 15' and 14'. It is to be understood that the masks regulate the size of the heart shapes, as explained hereinabove. It is also to be understood that the invention is not limited to the heart-shaped image, since any image can be produced in the stethoscope in accordance with the present invention.

Figure 7:
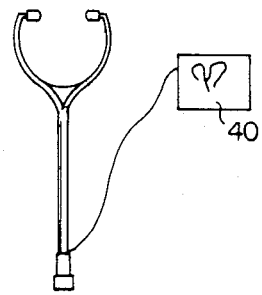
FIGS. 7-8 are views showing various inventive arrangements of an image display of the stehoscope in accordance with the invention.

FIG. 7 shows that the electronic device or at least a part of it does not have to be necessarily arranged in the end part 5. Instead, an additional member 40 is provided, which is located remotely from the end part and can contain at least the light emitting diodes with the light conductors and masks. Thus, the physician can unobjectionably monitor the heart activity of a patient by contacting the end part 5 of the stethoscope with the patients chest, while the patient can hold the member 40 in his or her hand and watch the image which changes in dependence on his heart activity. This is especially attractive for children.

Figure 8:
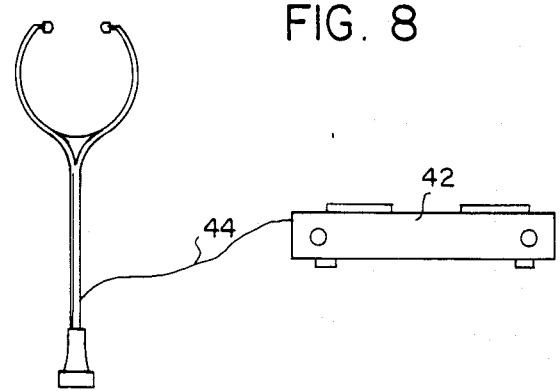

FIG. 8 shows that the stethoscope of the invention can be connected by a signal transmitting cable 44 with a recording and reproducing device of a known construction, instead of being connected with the diodes, liquid crystal display, screen. In this case the data of the patients heart activity are stored and can be reproduced for thorough analysis by the physician.

Also other possibilities of processing and utilization of the audio, video and electronic data obtained by the inventive stethoscope are possible.

The invention is not limited to the details shown since various modifications and structural changes are possible without departing in any way from the spirit of the present invention.

What is desired to be protected by Letters Patent is set forth in particular in the appended claims.

I claim:

1. A stethoscope, comprising
earphones; a tube; a body part connected by said tube with said earphones and having a passage for transferring sound from said body part to said tube; means forming a display in said body part; and electronic means forming on said display an image in the shape of a solid periodically expanding and contracting heart.

2. A stethoscope as defined in claim 1; and further comprising means forming an additional display, said electronic means being connected with said additional display so as to form also on said additional display image of a periodically expanding and contracting heart.

3. A stethoscope as defined in claim 2, wherein said first-mentioned display is located so that it is visible by a person who monitors heart beat with the stethoscope, whereas said additional display is located so that it is visible by a person whose heart beat is monitored by the stethoscope.

4. A stethoscope as defined in claim 1; and further comprising an additional member connected with and located at a distance from said body part, said display being formed on said additional remotely located member.

5. A stethoscope as defined in claim 1; and further comprising means for sensing heart beat and connected with said electronic means so that the image of a solid periodically expanding and contracting heart is formed on said display in response to the heart beat sensed by said sensing means.

6. A stethoscope as defined in claim 5, wherein said sensing means includes a microphone arranged to detect audio signals of the heart beat and transform the same into electronic signals to be supplied to said electronic means.

7. A stethoscope as defined in claim 1; and further comprising additional electronic means which generate audio signals imitating sounds of heart beats.

8. A stethoscope as defined in claim 7, wherein said further electronic means includes a sensor arranged to sense heart beats, and a generator arranged to generate said audio signals in response to the sensing of the heart beats by said sensing means.

9. A stethoscope as defined in claim 8, wherein said sensor is formed as a microphone arranged to detect audio signals of the heart beat and transform the same into electronic signals, and means for transmitting the latter to said generator.

10. A stethoscope as defined in claim 1; and further comprising means for detecting audio signals of heart beat and means for transmitting said signals for subsequent recording and reproduction.

11. A stethoscope as defined in claim 10; and further comprising recording and reproducing means connected with said transmitting means and receiving said audio signals from the latter for subsequent recording and reproducing.

12. A stethoscope, comprising earphones; a tube; a body part connected by said tube with said earphones and having a passage for transferring sound from said body to said tube; means forming a display including at least two elements overlapping one another and having a smaller size and a greater size; and electronic means connected with said display and operative for periodically illuminating at least one of said elements so as to form on said display the image of solid periodically expanding and contracting heart.

13. A stethoscope as defined in claim 12, wherein said electronic means includes means for alternatively illuminating said elements one after the other.

14. A stethoscope as defined in claim 12, wherein said elements are transparent, said electronic means including two light-emitting diodes, and means for periodically activating one of said light-emitting diodes and constantly activating the other of said light-emitting diodes so as to periodically illuminate one of said transparent elements and constantly illuminate the other of said transparent elements.

15. A stethoscope as defined in claim 1, wherein said display includes liquid crystals, said electronic means being operative for activating said liquid crystals so as to form on said display the image of a solid periodically expanding and contracting heart.

16. A stethoscope as defined in claim 12, wherein each of said elements has a shape of a heart so that said display has a smaller heart-shaped element and a greater heart-shaped element.

* * * * *